| United States Patent [19] | [11] Patent Number: 4,731,394 |
|---|---|
| Vogel et al. | [45] Date of Patent: Mar. 15, 1988 |

[54] INORGANIC-ORGANIC COMPOUND SUBSTANCES FOR BIOMEDICAL PURPOSES

[75] Inventors: Werner Vogel; Guenther Heublein; Wolfram Hoeland; Manfred Boese; Karin Naumann; Gunter Carl; Juergen Vogel; Peter Wange, all of Jena; Jens Gummel, Berlin; Peter Zinner, Jena; Eggert Beleites, Maua; Thomas Schubert, Dresden, all of German Democratic Rep.

[73] Assignee: Friedrich-Schiller-Universitaet Jena, Jena, German Democratic Rep.

[21] Appl. No.: 873,566

[22] Filed: Jun. 12, 1986

[30] Foreign Application Priority Data

Jun. 24, 1985 [DD] German Democratic Rep. ................ 2776665

[51] Int. Cl.$^4$ .................. C08K 3/40; C08K 9/04; C08K 9/06
[52] U.S. Cl. .................. 523/115; 523/113; 523/114; 523/116; 523/216; 523/217; 523/443; 523/444; 523/451; 523/458; 523/459; 523/466
[58] Field of Search ............... 523/113, 114, 115, 116, 523/217, 216, 443, 444, 451, 458, 459, 466

[56] References Cited

U.S. PATENT DOCUMENTS

| 3,400,097 | 9/1968 | Weinstein et al. | 523/116 |
|---|---|---|---|
| 3,808,170 | 4/1974 | Rogers | 523/466 |
| 3,973,972 | 8/1976 | Muller | 523/116 |
| 4,013,610 | 3/1977 | Tomohiro et al. | 523/217 |
| 4,131,597 | 12/1978 | Blüethgen et al. | 523/115 |
| 4,215,033 | 7/1980 | Bowen | 523/115 |
| 4,308,014 | 12/1981 | Kawahara et al. | 523/115 |
| 4,381,918 | 5/1983 | Ehrnford | 523/116 |
| 4,548,959 | 10/1985 | Nagiu et al. | 523/451 |
| 4,560,715 | 12/1985 | Veeda et al. | 523/443 |
| 4,605,570 | 8/1986 | Felter et al. | 523/451 |

FOREIGN PATENT DOCUMENTS 0149389 11/1981 Japan .................. 523/115

Primary Examiner—John C. Bleutge
Assistant Examiner—David W. Woodward
Attorney, Agent, or Firm—Jordan and Hamburg

[57] ABSTRACT

The invention relates to inorganic-organic compound substances useful for biomedical purposes. The object of the invention is to develop inorganic-organic compound materials which overcome the disadvantages of the state of art, wherein inorganic-organic compound substances for biomedical purposes possess to a large extent specifically adjustable characteristics. Inorganic initial substances form a new solid chemical compound with organic initial substances. The inorganic initial component consists of a biocompatible silicate glass and/or a silicate glass ceramic of the system $SiO_2$-$Al_2O_3$-$MgO$-$Na_2O/K_2O$-$F^-$, and/or a bioactive phosphate silicate glass and/or a phosphate silicate glass ceramic of the system $SiO_2$-$Al_2O_3$-$MgO$-$Na_2O/K_2O$-$CaO$-$P_2O_5F^-$ and/or of the system $SiO_2$-$MgO$-$K_2O$-$F^-$-$CaO$-$P_2O_5$, and/or a bioactive phosphate glass and/or a phosphate glass ceramic of the system $P_2O_5$-$Al_2O_3$-$CaO$-$Na_2O/K_2O$, and/or a sintred ceramic based upon tricalcium phosphate and/or apatite. The organic initial component consists of a biocompatible, monomer-free, epoxidized polymeric hydrocarbon consisting only of the elements C, H, O having an average molecular weight $\overline{Mn}$ of 2,000 to 6,000 and an epoxy equivalence EEW of 50 to 500 g. The inorganic initial component is modified by phosphoric acid.

11 Claims, No Drawings

INORGANIC-ORGANIC COMPOUND SUBSTANCES FOR BIOMEDICAL PURPOSES

The invention relates to inorganic-organic compound substances for biomedical purposes, which can be used, for example, in the form of moldable replacement for hard tissue or as an implant material having various characteristics.

BACKGROUND OF THE INVENTION AND RELATED ART STATEMENT

In human medicine materials are used to a great extent, for example, to embed endoprostheses or as polymerizing tooth filling materials, which represent low-molecular organic compounds and which polymerize into solid products after being introduced into the human body. Frequently, inorganic additive components are also added to the organic substances, so that composite materials result which, however, do not undergo any chemical bonding among each other. These materials have the disadvantage that in the first minutes after introduction into the body, nonreactive monomers can be transported away by the blood and can accumulate in certain organs of the body. Furthermore, during the process of the polymerization, inevitably, nonreacting monomers or oligomers remain in the hardened material and thus remain in the body, because it is not possible to carry out purifying operations, such as multistep extraction reactions and precipitation reactions as are carried out in organic chemistry. Consequently, for example, according to Schultz, Arch. Orthop. Unfall-Chir., 21 1971, 301-305, in the case of utilization of bone cement, based on methyl methacrylate, in addition to a decrease in blood pressure, there occur, above all, life-threatening immediate complications due to fat embolisms. Furthermore, according to T. Okano, Polym. Journal, 10, 233 (1987), proteins are adsorbed on the hydrophilic structural units of the hardened materials which, according to M. Suzuki, J. Biomed. Mat. Res. 15, 697 (1981) can cause side-effects as serious as the formation of blood clots. Generally, similar reactions which cause physically damaging processes and which, therefore, do not assure the required high biocompatibility, can be expected of all organic or inorganic-organic substances based on low-molecular compounds and/or consisting of elements other than C, H, O.

This is the case, for example, in DE-OS 2,821,354. For instance, with some of the polymers mentioned in the above-mentioned Offenlegungsschrift, such as polyurethanes, polyamides or epoxy resins as biomaterials, there can result damaging influences on the biological medium because of unreacted isocyanate groups or oligomers formed.

In addition to the possible reactions of isocyanate groups with the body fluids, the body tissues, blood cells or individual proteins, from the polyurethanes, by means of hydrolysis, there result metabolites containing amino groups which, for example, in the case of the aromatic diamines, represent potential carcinogens. According to N. A. Mohamud, Physicochem. Aspects of Polymer Surfaces, Vol. 2, page 953, Plenum Press, New York, London, 1983, the oligomers are also capable of slowly diffusing on the surface of the material and can cause undesirable blood reactions. For extra-corporal applications, but also for polyurethane-based container material intended for implants, expensive extraction methods as well as surface modifications of the material are used. With increasing viscosity in the hardening process, due to the accompanying diffusion, there inherently remain in macromolecules unreacted functional groups which, in the course of time, due to diffusing-in of water or ions, react out of the liquor and free low-molecular substances having amido bonds or amine bonds. Nonwithstanding their potential toxicity, especially because of the strong basicity of amines and diamines, blood clotting is particularly furthered. For the same reason, amines should not be used as hardening components, for example, for epoxy resins because in case of long-term exposure, the hydrolytic or enzymatic break-down of such compounds cannot be ruled out and implies potential dangers.

SUMMARY OF THE INVENTION

The object of the invention is to provide inorganic-organic compound substances which overcome the disadvantages of the state of art. The object of the invention consists in developing inorganic-organic compound materials for biomedical purposes which have to a large extent specifically adjustable characteristics.

The object of the invention is solved in that inorganic initial materials form with organic initial materials a new solid chemical compound, whereby the inorganic initial component represents a biocompatible silicate glass and/or a silicate glass ceramic of the composition by weight %

| | |
|---|---|
| $SiO_2 =$ | 34-60 |
| $Al_2O_3 =$ | 21-36 |
| $MgO =$ | 8-17 |
| $R_2O =$ | 5-12 |
| $F^- =$ | 1-7 | wherein $R_2O$ represents the sum of 0-8 weight-% $Na_2O$ and 0-6 weight-% $K_2O$,
and/or the inorganic initial component is a bioactive phosphosilicate glass and/or a phosphosilicate glass ceramic (A) of the composition by weight %

| | |
|---|---|
| $SiO_2 =$ | 19-52 |
| $Al_2O_3 =$ | 12-23 |
| $MgO$ | 5-15 |
| $R_2O =$ | 3-10 |
| $CaO =$ | 9-30 |
| $P_2O_5$ | 4-24 |
| $F^- =$ | 0.5-7 | wherein $R_2O$ represents the sum of 0-8 weight-% $Na_2O$ and 0-8 weight-% $K_2O$, and/or the inorganic initial component is a bioactive phosphosilicate glass and/or a phosphosilicate glass ceramic (B) of the composition by weight %

| | |
|---|---|
| $SiO_2 =$ | 18-63 |
| $MgO =$ | 10-35 |
| $K_2O =$ | 3-10 |
| $F^- =$ | 4-9 |
| $CaO =$ | 1-30 |
| $P_2O_5 =$ | 1-30 | and/or the inorganic initial component is a bioactive phosphate glass and/or a phosphate glass ceramic of the composition by weight %

| | |
|---|---|
| $P_2O_5 =$ | 43-58 |

| | |
|---|---|
| -continued | |
| $Al_2O_3 =$ | 3-21 |
| $CaO =$ | 8-26 |
| $R_2O =$ | 10-25 | wherein $R_2O$ can contain up to 25 weight-% $Na_2O$ and up to 18 weight-% $K_2O$, and/or the inorganic initial component is a sintered ceramic on the basis of tricalcium phosphate and/or apatite and the organic initial component is a biocompatible, monomer-free, epoxidized polymeric hydrocarbon which is composed only of the elements C, H, O, and has an average molecular weight $\overline{Mn}$ of 2,000 to 6,000, epoxy equivalence EEW of 50 to 500 g and the inorganic initial component is a substance modified by phosphoric acid. Furthermore, it is possible that the inorganic initial component in the form of the silicate glass and/or the silicate glass ceramic can contain additive substances of up to 10 weight-%, such as, for example, FeO, $Fe_2O_3$, CaO, $P_2O_5$, BaO, and the inorganic initial component in the form of the bioactive phosphosilicate glass and/or the phosphosilicate glass ceramic (A) can contain additive substances of up to 10 weight-%, such as, for example, FeO, $Fe_2O_3$, BaO, $TiO_2$, and the inorganic initial component in the form of the bioactive phosphosilicate glass and/or the phosphosilicate glass ceramic (B) can contain additive substances of up to 6 weight-%, such as, for example, $Al_2O_3$, $TiO_2$, $ZrO_2$, $Na_2O$, and the inorganic initial component in the form of the bioactive phosphate glass and/or the phosphate glass ceramic can contain additive substances of up to 10 weight-%, such as, for example, $TiO_2$, $B_2O_3$, $F^-$, $SiO_2$, FeO, $Fe_2O_3$, MgO. The organic initial component according to the invention is a monomer-free, epoxidized polymeric hydrocarbon which consists only of the elements C, H, O, and has a molecular weight $\overline{Mn}$ of 2,000 to 6,000 and epoxy equivalence EEW of 100 to 500 g. Suitable additive substances for the organic initial component are for example, coloring components and/or antibiotics and/or components which contribute to increasing the hydrophilicity, such as, for example, poly(vinyl alcohol - acrylic acid) copolymers.

DETAILED DESCRIPTION OF THE PREFERRED EMBODIMENTS

The compound substances according to the invention consist of 20-70 weight-% of an organic initial component and 30-80 weight-% of an inorganic initial component whereby, due to an inventive 1-24 hour long treatment of the inorganic component with 30-50% $H_3PO_4$, at 25° to 130° C. and mixing of the two initial components, there are developed compound substances which have greatly varying characteristics, i.e., for example, exhibiting characteristics ranging from resembling cartilage to resembling bone. During the formation of these compound substances according to the invention, which are characterized by a strong chemical bond between inorganic and organic components, there never occur temperatures exceeding 45° C. Consequently, it allows the application as moldable replacement for hard tissue, for example, for the embedding of endoprotheses, or for the substitution of bone defects or as replacement material for cartilage.

Furthermore, it is surprising that according to the invention, it is possible to develop implants having long-term stability and various mechanical parameters, such as, for example, strength and E-modulus, which can be specifically adjusted, for example, ranging from resembling cartilage to resembling bone. According to the invention, by means of production outside of the biological medium, the reaction time can be shortened by increasing the reaction temperature, for example, to 100° C.

Because of the adjustable characteristics, the very good biocompatibility and bioactivity, it is possible to produce implants for almost all parts of the human body. According to the invention, a fast, 80% hardening can be attained in approximately 20 minutes by means of a 12-hour long treatment of the inorganic initial component with 50% $H_3PO_4$ at 110° C. and reactions with the organic component, so that the substances according to the invention can be used, for example, as tooth filling material or dental products, such as, for example, tooth structures, also in combination with high-strength base materials.

Especially advantageous bioactive characteristics are possessed, for example, by compound substances according to the invention which contain as the inorganic initial component bioactive glass ceramics which have the main crystal phases mica and apatite. The reason is that the inorganic component forms a direct bond with the living bone at only a minimum reaction zone of 5 to 12 µm. This material characteristic is of decisive importance for the application of the compound substances according to the invention as a moldable replacement for hard tissue, because the optimum grain size of the organic initial component for this application is 40 to 460 µm. In other known bioactive glass ceramics there occur reaction zones at the surface of the glass ceramic which are greater than 150 µm, so that it results in a considerable reduction of strength of the compound of glass ceramic and bone and, above all, in the dissolution of the material in a layer thickness of more than 150 µm, i.e., particles of less than 150 µm are being dissolved.

Because the reaction zone between the inorganic component of the compound substances according to the invention and the living bone is only 5 to 12 µm, the particles are preserved and mainly from the apatite crystals there emanates the bioactive characteristic for the compound formation with the living bone. In summary, this means that the inorganic and the organic components, by means of the formation of a direct chemical bond, result in the compound substances according to the invention and that, emanating from the inorganic component a bond with the bone is attained.

EXAMPLE 1

The inorganic initial material, which consists, for example, of a glass ceramic having a main crystal phase apatite and mica, is treated with a 50% phosphoric acid at 110° C. and the excess liquid is separated in appropriate form. 55 weight parts of the thus obtained treated inorganic initial material are intensively mixed with 45 weight parts of an epoxidized polymeric hydrocarbon of an average molecular weight of $\overline{Mn}$ 3,700 and an epoxy equivalence weight EEW of 156 g. After 15 minutes, the mass is hardened and attains 80% of its hardness. After 24 hours, the compound substances according to the invention have attained their final hardness.

EXAMPLE 2

The inorganic initial material, which consists, for example, of a glass ceramic, which contains mica as the main crystal phase, is treated with 30% phosphoric acid for 12 hours at 25° C., the excess liquid removed, and then is mixed with the organic component at a ratio of one part of inorganic component to 2 parts of organic component. 30 minutes after the mixing, this material is still moldable, and after 2 hours, it has elasticity-to-compression characteristics and strength values resembling cartilage.

The epoxidized hydrocarbon has an average molecular weight $\overline{Mn}$ of 3,700 and an epoxy equivalence weight EEW of 250 g.

EXAMPLE 3

The inorganic initial material, which consists, for example, of a mica glass ceramic, is treated with 50% phosphoric acid for 12 hours at 110° C. and the excess liquid is removed. The thus treated inorganic initial material is mixed with equal parts of an epoxidized polymeric hydrocarbon, which has an average molecular weight Mn of 5,600 and an epoxy equivalence weight EEW of 110 g. The compound substance according to the invention is hardened after 20 minutes and attains in this time period 80% of its final hardness, which is attained after 24 hours.

EXAMPLE 4

60 weight parts of the treated inorganic component according to Example 1 are intensely mixed and hardened in an appropriate form after degasification at 80° C. in 3 hours. The thus obtained testing bodies having the size of 2×2×2 mm or 5×5×35 mm of the reaction composites obtained according to the method according to Examples 1-3 have been tested with respect to their mechanical strength and toxicological harmlessness. Thereby it was possible to attain bending strengths of up to 180 MPa and E-moduli of up to $2.3 \times 10^4$. Not only the initial components, but also the test bodies, for instance, reduced to small pieces, did not exhibit any disadvantages in comparison to recognized biocompatibility norms, for example, on cell cultures.

The evaluation of partially experimental tests shows a connective-tissue-free binding of the compound substances according to the invention with bioactive components.

Table 1 shows the compositions in weight-% and main crystal phases of the inorganic initial components of the compound substances according to the invention.

TABLE 1

| | 1 | 2 | 3 | 4 | 5 | 6 |
|---|---|---|---|---|---|---|
| $SiO_2$ | — | — | — | 39.4 | 48.4 | 36.0 |
| $Al_2O_3$ | 20.9 | 12.9 | 8.8 | — | 29.1 | 20.0 |
| MgO | — | — | — | 25.5 | 12.6 | 10.9 |
| $Na_2O$ | 15.9 | 16.8 | 14.3 | — | 3.2 | 2.3 |
| $K_2O$ | — | — | — | 6.9 | 4.3 | 3.9 |
| CaO | 14.0 | 14.1 | 15.6 | 9.9 | — | 12.5 |
| $P_2O_5$ | 49.2 | 49.6 | 50.2 | 10.1 | — | 9.5 |
| $F^-$ | — | 1.7 | 1.8 | 6.4 | 2.7 | 4.9 |
| FeO | — | 4.5 | 3.7 | — | — | — |
| $Fe_2O_3$ | — | 0.4 | — | — | — | — |
| $TiO_2$ | — | — | 5.6 | 2.0 | — | — |
| main crystal phase | OH apatite $AlPO_4$ phosphate mixing phase | F-apatite phase of the berlinite-type phosphate mixing phase | F-apatite $AlPO_4$ (berlinite) phosphate mixing phase | mica apatite | mica | mica apatite |

What we claim is:

1. Inorganic-organic compound substances useful for biomedical purposes, comprising 30 to 80 weight-% of an inorganic initial material chemically bonded with 20 to 70 weight-% of an organic initial material, wherein the inorganic initial material is selected from the group consisting of a biocompatable silicate glass, silicate glass ceramic or mixtures thereof having a composition by weight % of

| | |
|---|---|
| $SiO_2$ = | 34-60 |
| $Al_2O_3$ = | 21-36 |
| MgO = | 8-17 |
| $R_2O$ = | 5-12 |
| $F^-$ = | 1-7 | wherein $R_2O$ represents the sum of 0-8 weight-% $Na_2O$ and 0-6 weight-% $K_2O$,
a bioactive phosphosilicate glass, a phosphosilicate glass ceramic (A) or mixtures thereof having a composition by weight % of

| | |
|---|---|
| $SiO_2$ = | 19-52 |
| $Al_2O_3$ = | 12-23 |
| MgO | 5-15 |
| $R_2O$ = | 3-10 |
| CaO = | 9-30 |
| $P_2O_5$ | 4-24 |
| $F^-$ = | 0.5-7 | wherein $R_2O$ represents the sum of 0-8 weight-% $Na_2O$ and 0-8 weight-% $K_2O$,
a bioactive phosphosilicate glass, a phosphosilicate glass ceramic (B) or mixtures thereof having a composition by weight % of

| | |
|---|---|
| $SiO_2$ = | 18-63 |
| MgO = | 10-35 |
| $K_2O$ = | 3-10 |
| $F^-$ = | 4-9 |
| CaO = | 1-30 |
| $P_2O_5$ = | 1-30 | a bioactive phosphate glass, a phosphate glass ceramic or mixtures thereof having a composition by weight % of

| | |
|---|---|
| $P_2O_5$ = | 43-58 |
| $Al_2O_3$ = | 3-21 |
| CaO = | 8-26 |
| $R_2O$ = | 10-25 | wherein $R_2O$ can contain up to 25 weight-% $Na_2O$ and up to 18 weight-% $K_2O$,
a sintered ceramic comprising tricalcium phosphate apatite or mixtures thereof and mixtures thereof, and the organic initial material comprises a biocompatible, monomer-free, epoxidized polymeric hydrocarbon composed only of the elements C, H, O having an average molecular weight $\overline{Mn}$ of 2,000 to 6,000 and an epoxy equivalence EEW of 50 to 500 g, wherein the inorganic initial material has been pretreated with phosphoric acid to facilitate said chemical bonding between the organic and inorganic initial materials.

2. Inorganic-organic compound substances according to claim 1, wherein the inorganic initial material comprises said silicate glass, silicate glass ceramic or mixtures thereof and additionally contains up to 10 weight-% of an additive selected from the group consisting of FeO, $Fe_2O_3$, CaO, $P_2O_5$, BaO and mixtures thereof.

3. Inorganic-organic compound substances according to claim 1, wherein the inorganic initial material comprises said bioactive phosphosilicate glass, phosphate silicate glass ceramic (A) or mixtures thereof and additionally contains up to 10 weight-% of an additive selected from the group consisting of FeO, $Fe_2O_3$, BaO, $TiO_2$ and mixtures thereof.

4. Inorganic-organic compound substances according to claim 1, wherein the inorganic initial material comprises said bioactive phosphate silicate glass, phosphosilicate glass ceramic (B) or mixtures thereof and additionally contains up to 6 weight-% of an additive selected from the group consisting of $Al_2O_3$, $TiO_2$, $ZrO_2$, $Na_2O$ and mixtures thereof.

5. Inorganic-organic compound substances according to claim 1, wherein the inorganic initial material comprises said bioactive phosphate glass, phosphate glass ceramic or mixtures thereof and additionally contains up to 10 weight-% of an additive selected from the group consisting of $TiO_2$, $B_2O_3$, $F^-$, $SiO_2$, FeO, $Fe_2O_3$, MgO and mixture thereof.

6. Inorganic-organic compound substances according to claim 1, wherein said inorganic initial material contains main crystal phases selected from the group consisting of mica, apatite, apatite and $SiO_2$-isotype crystals and mixtures thereof.

7. Inorganic-organic compound substances according to claim 1, wherein the organic initial material contains additives selected from the group consisting of coloring components, antibiotics, hydrophilicity increasing components and mixtures thereof.

8. Inorganic-organic compound substances according to claim 7, wherein said hydrophilicity-increasing components comprise poly(vinyl alcohol-acrylic acid) copolymers.

9. A method of producing inorganic-organic compound substances useful for biomedical purposes, comprising
treating an inorganic initial material with 30 to 50% $H_3PO_4$ for 1 to 24 hours at 25° to 130° C., said inorganic initial material being selected from the group consisting of a biocompatible silicate glass, a silicate glass ceramic or mixtures thereof having a composition by weight % of

| | |
|---|---|
| $SiO_2 =$ | 34–60 |
| $Al_2O_3 =$ | 21–36 |
| MgO = | 8–17 |
| $R_2O =$ | 5–12 |
| $F^- =$ | 1–7 | wherein $R_2O$ represents the sum of 0–8 weight-% $Na_2O$ and 0–6 weight-% $K_2O$,
a bioactive phosphosilicate glass, a phosphosilicate glass ceramic (A) or mixtures thereof having a composition by weight % of

| | |
|---|---|
| $SiO_2 =$ | 19–52 |
| $Al_2O_3 =$ | 12–23 |
| MgO | 5–15 |
| $R_2O =$ | 3–10 |
| CaO = | 9–30 |
| $P_2O_5$ | 4–24 |
| $F^- =$ | 0.5–7 | wherein $R_2O$ represents the sum of 0–8 weight-% $Na_2O$ and 0–8 weight-% $K_2O$,
a bioactive phosphosilicate glass, a phosphosilicate glass ceramic (B) or mixtures thereof having a composition by weight % of

| | |
|---|---|
| $SiO_2 =$ | 18–63 |
| MgO = | 10–35 |
| $K_2O =$ | 3–10 |
| $F^- =$ | 4–9 |
| CaO = | 1–30 |
| $P_2O_5 =$ | 1–30 | a bioactive phosphate glass, a phosphate glass ceramic or mixtures thereof having a composition by weight % of

| | |
|---|---|
| $P_2O_5 =$ | 43–58 |
| $Al_2O_3 =$ | 3–21 |
| CaO = | 8–26 |
| $R_2O =$ | 10–25 | wherein $R_2O$ can contain up to 25 weight-% $Na_2O$ and up to 18 weight-% $K_2O$,
a sintered ceramic comprising tricalcium phosphate, apatite and mixtures thereof;
mixing 30 to 80 weight-% of said treated inorganic initial material with 20 to 70 weight-% of an organic initial material comprising a biocompatible, monomer-free, epoxidized polymeric hydrocarbon composed only of the elements C, H, O having an average molecular weight $\overline{Mn}$ of 2,000 to 6,000 and an epoxy equivalence EEW of 50 to 500 g, at a temperature of 45° C. or less, to form a final reacted and chemically bonded inorganic-organic material resembling bone or cartilage suitable for endoprostheses, bone defect substitutions and body cartilage replacements, whereby said treatment with $H_3PO_4$ facilitates said chemical bonding.

10. A method for producing inorganic-organic compound substances useful for biomedical purposes, comprising
treating an inorganic initial material with 30 to 50% $H_3PO_4$ for 1 to 24 hours at 25° to 130° C., said inorganic initial material being selected from the group consisting of a biocompatible silicate glass, a silicate glass ceramic or mixtures thereof having a composition by weight % of

| | |
|---|---|
| $SiO_2 =$ | 34–60 |
| $Al_2O_3 =$ | 21–36 |
| MgO = | 8–17 |
| $R_2O =$ | 5–12 |
| $F^- =$ | 1–7 | wherein $R_2O$ represents the sum of 0–8 weight-% $Na_2O$ and 0–6 weight-% $K_2O$,
a bioactive phosphosilicate glass, a phosphosilicate glass ceramic (A) or mixtures thereof having a composition by weight % of

| | |
|---|---|
| $SiO_2 =$ | 19–52 |
| $Al_2O_3 =$ | 12–23 |
| MgO | 5–15 |
| $R_2O =$ | 3–10 |
| CaO = | 9–30 |
| $P_2O_5$ | 4–24 |

-continued

| | |
|---|---|
| F$^-$ = | 0.5–7 | wherein R$_2$O represents the sum of 0–8 weight-% Na$_2$O and 0–8 weight-% K$_2$O, a bioactive phosphosilicate glass, a phosphosilicate glass ceramic (B) or mixtures thereof having a composition by weight % of

| | |
|---|---|
| SiO$_2$ = | 18–63 |
| MgO = | 10–35 |
| K$_2$O = | 3–10 |
| F$^-$ = | 4–9 |
| CaO = | 1–30 |
| P$_2$O$_5$ = | 1–30 | a bioactive phosphate glass, a phosphate glass ceramic or mixtures thereof having a composition by weight % of

| | |
|---|---|
| P$_2$O$_5$ = | 43–58 |
| Al$_2$O$_3$ = | 3–21 |
| CaO = | 8–26 |
| R$_2$O = | 10–25 | wherein R$_2$O can contain up to 25 weight-% Na$_2$O and up to 18 weight-% K$_2$O, a sintered ceramic comprising tricalcium phosphate, apatite and mixtures thereof;

mixing 30 to 80 weight-% of said inorganic initial material with 20 to 70 weight-% of an organic initial material comprising a biocompatible, monomer-free, epoxidized polymeric hydrocarbon composed only of the elements C, H, O having an average molecular weight $\overline{\text{Mn}}$ of 2,000 to 6,000 and an epoxy equivalence EEW of 50 to 500 g, to form a reacted and chemically bonded inorganic-organic material, whereby said treatment with H$_3$PO$_4$ facilitates said chemical bonding; and hardening said reacted inorganic-organic material to a particular shape at 25° to 100° C. to attain an implant material having long-term stability and various bioactive or biocompatible characteristics.

11. A method of producing inorganic-organic compound substances useful for biomedical purposes, comprising treating an inorganic initial material with 50% H$_3$PO$_4$ for 12 hours at 110° C., said inorganic initial material being selected from the group consisting of a biocompatible silicate glass, a silicate glass ceramic or mixtures thereof having a composition by weight % of

| | |
|---|---|
| SiO$_2$ = | 34–60 |
| Al$_2$O$_3$ = | 21–36 |
| MgO = | 8–17 |

-continued

| | |
|---|---|
| R$_2$O = | 5–12 |
| F$^-$ = | 1–7 | wherein R$_2$O represents the sum of 0–8 weight-% Na$_2$O and 0–6 weight-% K$_2$O, a bioactive phosphosilicate glass, a phosphosilicate glass ceramic (A) or mixtures thereof having a composition by weight % of

| | |
|---|---|
| SiO$_2$ = | 19–52 |
| Al$_2$O$_3$ = | 12–23 |
| MgO | 5–15 |
| R$_2$O = | 3–10 |
| CaO = | 9–30 |
| P$_2$O$_5$ | 4–24 |
| F$^-$ = | 0.5–7 | wherein R$_2$O represents the sum of 0–8 weight-% Na$_2$O and 0–8 weight-% K$_2$O, a bioactive phosphosilicate glass, a phosphosilicate glass ceramic (B) or mixtures thereof having a composition by weight % of

| | |
|---|---|
| SiO$_2$ = | 18–63 |
| MgO = | 10–35 |
| K$_2$O = | 3–10 |
| F$^-$ = | 4–9 |
| CaO = | 1–30 |
| P$_2$O$_5$ = | 1–30 | a bioactive phosphate glass, a phosphate glass ceramic or mixtures thereof having a composition by weight % of

| | |
|---|---|
| P$_2$O$_5$ = | 43–58 |
| Al$_2$O$_3$ = | 3–21 |
| CaO = | 8–26 |
| R$_2$O = | 10–25 | wherein R$_2$O can contain up to 25 weight-% Na$_2$O and up to 18 weight-% K$_2$O, a sintered ceramic comprising tricalcium phosphate, apatite and mixtures thereof;

mixing 30 to 80 weight-% of said inorganic initial material with 20 to 70 weight-% of an organic initial material comprising a biocompatible, monomer-free, epoxidized polymeric hydrocarbon composed only of the elements C, H, O having an average molecular weight $\overline{\text{Mn}}$ of 2,000 to 6,000 and an epoxy equivalence EEW of 50 to 500 g, to form a reacted and chemically bonded inorganic-organic material hardening to within 80% of final hardness within 20 minutes after mixing suitable for use as a tooth filling material and tooth structure material, whereby said treatment with H$_3$PO$_4$ facilitates said chemical bonding.

* * * * *